United States Patent
Usui et al.

(10) Patent No.: US 10,435,444 B2
(45) Date of Patent: Oct. 8, 2019

(54) AGENT FOR PREVENTION OR TREATEMENT OF CORNEAL DISORDERS

(71) Applicants: The University of Tokyo, Tokyo (JP); Senju Pharmaceutical Co., Ltd., Chuo-ku, Osaka-shi, Osaka (JP)

(72) Inventors: Tomohiko Usui, Tokyo (JP); Chiho Yabuta, Osaka (JP)

(73) Assignees: THE UNIVERSITY OF TOKYO, Tokyo (JP); SENJU PHARMACEUTICAL CO., LTD., Osaka-Shi (JP)

( * ) Notice: Subject to any disclaimer, the term of this patent is extended or adjusted under 35 U.S.C. 154(b) by 0 days.

(21) Appl. No.: 15/566,640

(22) PCT Filed: Apr. 15, 2016

(86) PCT No.: PCT/JP2016/062168
§ 371 (c)(1),
(2) Date: Oct. 13, 2017

(87) PCT Pub. No.: WO2016/167363
PCT Pub. Date: Oct. 20, 2016

(65) Prior Publication Data
US 2018/0105563 A1    Apr. 19, 2018

(30) Foreign Application Priority Data

Apr. 17, 2015 (JP) ................. 2015-085010

(51) Int. Cl.
| | | |
|---|---|---|
| A61K 38/00 | (2006.01) | |
| C07K 14/47 | (2006.01) | |
| A61P 27/02 | (2006.01) | |
| A61K 9/00 | (2006.01) | |
| A61K 38/17 | (2006.01) | |

(52) U.S. Cl.
CPC ........ *C07K 14/4705* (2013.01); *A61K 9/0048* (2013.01); *A61K 38/1709* (2013.01); *A61P 27/02* (2018.01)

(58) Field of Classification Search
None
See application file for complete search history.

(56) References Cited

FOREIGN PATENT DOCUMENTS

| EP | 2 157 082 A1 | 2/2010 |
|---|---|---|
| JP | 2005-213159 A | 8/2005 |
| WO | WO-01/29085 A2 | 4/2001 |

OTHER PUBLICATIONS

Written Opinion dated Jun. 14, 2016 in International Application PCT/JP2016/062168.
Kuchtey et al., "Angiopoietin-like 7 Secretion Is Induced by Glaucoma Stimuli and Its Concentration is Elevated in Glaucomatous Aqueous Humor," Investigative Ophthalmology & Visual Science (Aug. 2008) vol. 49(8) pp. 3438-3448.
Mathers, "Why the Eye Becomes Dry: A cornea and Lacrimal Gland Feedback Model," The CLAO Journal (Jul. 2000) vol. 26(3) pp. 159-165.
Peek et al., "Molecular Cloning of a New Angiopoietinlike Factor from the Human Cornea," Investigative Ophthalmology & Visual Science (Sep. 1998) vol. 39(10) pp. 1782-1788.
Toyono et al., "Angiopoitin-like 7 is an Anti-Angiogenic Protein Required to Prevent Vascularization of the Cornea," PLOS One, (Jan. 2015) vol. 10(1) pp. 1-13.
Tetsuya et al., "Angiopoietin like protein 7 is a novel anti-angiogenic molecule expressed in cornea," Annual Meeting of the Association-for-Research in-Vision-and-Ophthalmology (ARVO), vol. 55, No. 13, p. 3244 (Apr. 2014), XP002785707.
Extended European Search Report dated Nov. 6, 2018 in European Application 16780154.7.

*Primary Examiner* — Jeanette M Lieb
(74) *Attorney, Agent, or Firm* — Foley & Lardner LLP

(57) ABSTRACT

An object of the invention is to provide an agent for preventing or treating corneal disorders, such as corneal epithelial disorder, dry eye, and reduction in corneal sensitivity. This object is achieved by using angiopoietin-like protein 7 as an active ingredient.

17 Claims, 7 Drawing Sheets

Specification includes a Sequence Listing.

Observation region: 0.42 x 0.42 mm²
B: Two sites between the middle and the periphery of the cornea
(A total of eight sites in the entire cornea)

AGENT FOR PREVENTION OR TREATEMENT OF CORNEAL DISORDERS

TECHNICAL FIELD

The present invention relates to an agent for preventing or treating corneal disorders such as corneal epithelial disorder, dry eye, and reduction in corneal sensitivity. The present invention further relates to an agent for promoting corneal tissue repair and an agent for promoting neurite formation of the ophthalmic nerve.

BACKGROUND ART

Corneal tissue is damaged by various factors, such as internal factors including decreased amounts of tears, reduction in corneal sensitivity, diabetes, and microbial infection; and external factors including drugs, injury, contact lenses, and light. Corneal disorders caused by such damages can lead to blindness in severe cases, and even in mild cases, corneal disorders can become severe when the damaged site is infected with a microorganism. It is thus extremely important to perform appropriate treatment for corneal disorders, or prevent corneal disorders by removing internal factors.

Dry eye is a disease that leads to corneal disorders due to decreases in the amount of tears or changes in the quality of tears. In recent years, the number of dry eye patients has been growing with increases in, for example, VDT operations and contact lens wearers, and is said to have reached about 8 million including potential patients.

Reduction in corneal sensitivity is said to continue generally for about 3 weeks to 1 year after corneal surgeries such as photorefractive keratectomy (PRK), laser-assisted in situ keratomileusis (LASIK), laser assisted subepithelial keratectomy (LASIK), and corneal transplantation, because corneal nerves are severed by such surgeries. It is known that reduction in corneal sensitivity induces lacrimal hyposecretion, which leads to a corneal disorder, and ultimately causes a lacrimal gland disorder, and that these occur in a vicious cycle (NPL 1).

Angiopoietin-like proteins (ANGPTLs) are known as proteins structurally similar to angiopoietin. In humans, seven kinds of angiopoietin-like proteins have been identified to date. It has been reported that ANGPTL7, which is one of them, is expressed in the corneal stroma, the Bowman's membrane, the sclera, the Schlemm's canal endothelium, the trabecular meshwork, and the lamina cribrosa of the optic nerve in ocular tissue. It has been reported that ANGPTL7 have, for example, the following functions: ANGPTL7 is involved in maintaining the transparency of the cornea (NPL 2); ANGPTL7 is involved in tumor growth suppression and angiogenesis suppression (NPL 3); and that ANGPTL7 suppresses invasion of blood vessels into the cornea (NPL 4).

However, the effect of ANGPTL7 on corneal disorders such as corneal epithelial disorder, dry eye, and reduction in corneal sensitivity has not been known at all.

CITATION LIST

Patent Literature
 Non-Patent Literature
 NPL 1: Mathers W D, Why the eye becomes dry: a cornea and lacrimal gland feedback model. CLAO J. Vol. 26, No. 3 159-165 (2000)
 NPL 2: Ron Peek, B. Elske van Gelderen, Marcel Bruinenberg, Aize Kijlstra, Molecular Cloning of a New Angiopoietinlike Factor from the Human Cornea. Investigative Ophthalmology & Visual Science, Vol. 39, No. 10 1782-1788 (1998)
 NPL 3: John Kuchtey, Maria E. Kallberg, Kirk N. Gelatt, Tommy Rinkoski, András M. Komàromy, Rachel W. Kuchtey, Angiopoietin-like 7 Secretion Is Induced by Glaucoma Stimuli and Its Concentration Is Elevated in Glaucomatous Aqueous Humor. Ophthalmology & Visual Science, Vol. 49, No. 8 3438-3448 (2008)
 NPL 4: Tetsuya Toyono, Tomohiko Usui, Seiichi Yokoo, Yukako Taketani, Suguru Nakagawa, Masahiko Kuroda, Satoru Yamagami, Shiro Amano, Angiopoietin-Like 7 Is an Anti-Angiogenic Protein Required to Prevent Vascularization of the Cornea. PLoS ONE 10(1): e0116838. doi: 10.1371/journal.pone.0116838

SUMMARY OF INVENTION

Technical Problem
 An object of the present invention is to provide an agent for preventing or treating corneal disorders such as corneal epithelial disorder, dry eye, and reduction in corneal sensitivity.
Solution to Problem
 The present inventors conducted extensive research to achieve the above object, and found that angiopoietin-like protein 7 has an action of promoting corneal tissue repair and an action of promoting neurite formation of the ophthalmic nerve and further that angiopoietin-like protein 7 is useful for the prevention or treatment of corneal disorders such as corneal epithelial disorder, dry eye, and reduction in corneal sensitivity. The inventors further conducted extensive research based on these findings and accomplished the present invention.

More specifically, the present invention includes the following embodiments.

Item 1. An agent for preventing or treating a corneal disorder, comprising angiopoietin-like protein 7.

Item 1-1. Angiopoietin-like protein 7 for use as an agent for preventing or treating a corneal disorder.

Item 1-2. A method for preventing or treating a corneal disorder, comprising administering an angiopoietin-like protein to a patient.

Item 1-3. Use of an angiopoietin-like protein for the production of an agent for preventing or treating a corneal disorder.

Item 2. The agent according to any one of Item 1 and Items 1-1 to 1-3, wherein the corneal disorder is at least one member selected from the group consisting of corneal epithelial disorder, dry eye, and reduction in corneal sensitivity.

Item 3. An agent for promoting corneal tissue repair, comprising angiopoietin-like protein 7.

Item 3-1. Angiopoietin-like protein 7 for use as an agent for promoting corneal tissue repair.

Item 3-2. A method for promoting corneal tissue repair, comprising administering an angiopoietin-like protein to a patient.

Item 3-3. Use of an angiopoietin-like protein for the production of an agent for promoting corneal tissue repair.

Item 4. The agent according to any one of Item 3 and Items 3-1 to 3-3, wherein the corneal tissue is at least one member selected from the group consisting of the corneal epithelium and corneal nerves.

Item 5. An agent for promoting neurite formation of the ophthalmic nerve, comprising angiopoietin-like protein 7.

Item 5-1. Angiopoietin-like protein 7 for use as an agent for promoting neurite formation of the ophthalmic nerve.

Item 5-2. A method for promoting neurite formation of the ophthalmic nerve, comprising administering an angiopoietin-like protein to a patient.

Item 5-3. Use of an angiopoietin-like protein for the production of an agent for promoting neurite formation of the ophthalmic nerve.

Item 6. The agent according to any one of Item 5 and Items 5-1 to 5-3, wherein the ophthalmic nerve is corneal nerves.

Item 7. An ophthalmic composition comprising angiopoietin-like protein 7.

Advantageous Effects of Invention

According to the present invention, an agent for preventing or treating corneal disorders such as corneal epithelial disorder, dry eye, and reduction in corneal sensitivity can be provided by using angiopoietin-like protein 7 as an active ingredient. An agent for preventing or treating other various diseases can also be provided based on the functions of angiopoietin-like protein 7 (action of promoting corneal tissue repair and action of promoting neurite formation of the ophthalmic nerve).

BRIEF DESCRIPTION OF DRAWINGS

FIG. 2 also shows immunostaining images of the cornea obtained using an anti-β3 tubulin antibody five days after abrasion of the corneal epithelium (Test Example 2) (lower portion: photographs).

DESCRIPTION OF EMBODIMENTS

Figure 1:
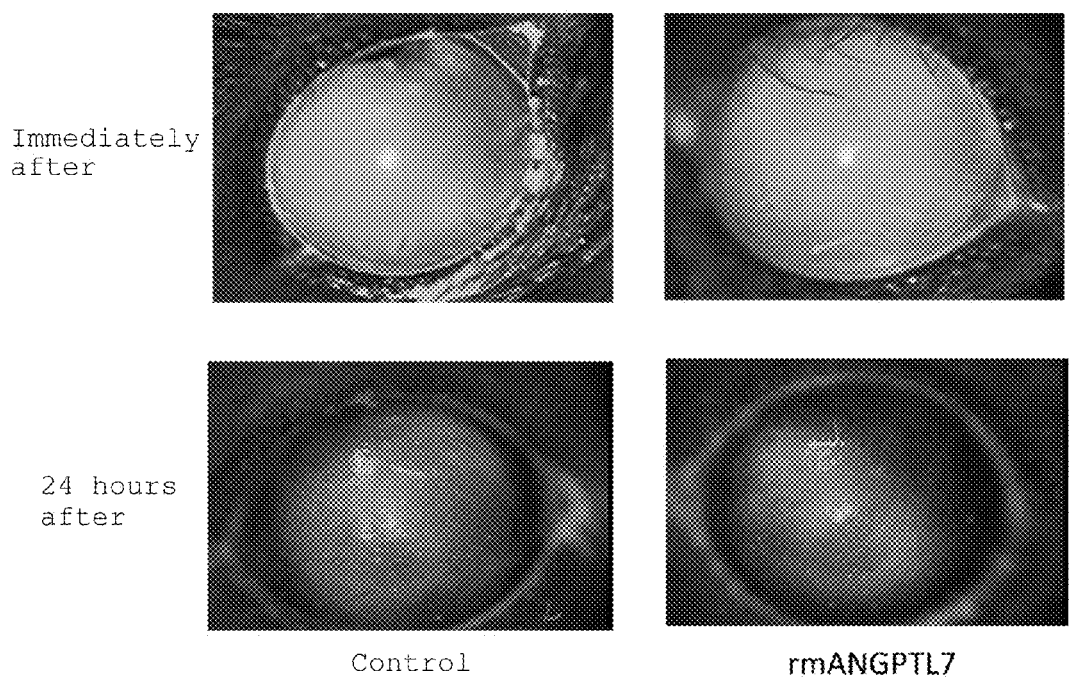
FIG. 1 shows fluorescein staining images of eyeballs immediately after abrasion of the corneal epithelium and 24 hours after abrasion of the corneal epithelium (Test Example 1).

The present invention relates to an agent for preventing or treating corneal disorders, an agent for promoting corneal tissue repair, an agent for promoting neurite formation of the ophthalmic nerve, or an ophthalmic composition, all of which comprise angiopoietin-like protein 7 (which may be referred to herein as "ANGPTL7") (these agents and composition may be collectively referred to herein as "the agent of the present invention"). The agent of the present invention is described below.

As its name implies, ANGPTL7 (angiopoietin-like protein or angiopoietin-related protein) is a kind of protein similar to angiopoietin (ANGPTL; in humans, seven kinds of ANGPTLs, i.e., ANGPTL1 to ANGPTL7, have been identified) and is a protein expressed in ocular tissue such as the cornea. Examples of usable ANGPTL7 include ANGPTL7 derived from various mammals including humans, monkeys, mice, rats, dogs, cats, and rabbits. Of these, ANGPTL7 derived from the organism species of an administration subject is preferable.

The amino acid sequences of ANGPTL7 derived from a variety of organism species are known. More specifically, human ANGPTL7 is, for example, a protein consisting of the amino acid sequence set forth in SEQ ID NO: 1 (NCBI Reference Sequence: NP_066969.1), and mouse ANGPTL7 is, for example, a protein consisting of the amino acid sequence set forth in SEQ ID NO: 2 (NCBI Reference Sequence: NP_001034643.1).

ANGPTL7 is preferably at least one protein selected from the group consisting of proteins set forth in the following (a) and (b):

(a) a protein consisting of the amino acid sequence set forth in SEQ ID NO: 1 or 2, (b) a protein consisting of an amino acid sequence having at least 85% identity to the amino acid sequence set forth in SEQ ID NO: 1 or 2, the protein having an action of promoting corneal tissue repair and/or an action of promoting neurite formation of the ophthalmic nerve.

The "identity" between amino acid sequences refers to the degree of identical amino acid sequences between two or more comparable amino acid sequences. Accordingly, when the identity between two amino acid sequences is high, the identity or similarity of these sequences is high. The level of identity between amino acid sequences is determined, for example, using FASTA, which is a sequence analysis tool, based on default parameters. Alternatively, it can be determined using the algorithm BLAST of Karlin and Altschul (KarlinS, Altschul S F. "Methods for assessing the statistical significance of molecular sequence features by using general scoring schemes" Proc. Natl Acad Sci USA. 87:2264-2268 (1990); and KarlinS, Altschul S F. "Applications and statistics for multiple high-scoring segments in molecular sequences." Natl Acad Sci USA. 90:5873-7(1993)). Programs such as BLASTX based on the BLAST algorithm described above have been developed. Specific techniques of these analysis methods are known. Reference may be made to the website of the National Center of Biotechnology Information (NCBI) (http://www.ncbi.nlm.nih.gov/).

In (b) above, the identity is preferably 90% or more, more preferably 95% or more, and even more preferably 98% or more.

The presence or absence of an action of promoting corneal tissue repair can be determined according to the methods described later in Test Example 1 and Test Example 2. In addition, the presence or absence of an action of promoting neurite formation of the ophthalmic nerve can be determined according to the method described later in Test Example 3.

The following is an example of the protein set forth in (b) above:

(b') a protein consisting of the amino acid sequence set forth in SEQ ID NO: 1 or 2 in which one or a plurality of amino acids are substituted, deleted, added, or inserted, the protein having an action of promoting corneal tissue repair and/or an action of promoting neurite formation of the ophthalmic nerve.

In (b'), the plurality of amino acids are, for example, 2 to 50 amino acids, preferably 2 to 30 amino acids, more preferably 2 to 15 amino acids, even more preferably 2 to 10 amino acids, even still more preferably 2 to 5 amino acids, and even still further more preferably 2 or 3 amino acids.

In the proteins set forth in (b) and (b') above, the mutation(s) are preferably conservative substitution(s). The conservative substitution means that an amino acid residue is replaced with an amino acid residue having a similar side chain.

For example, a substitution between amino acid residues with basic side chains, such as lysine, arginine, and histidine, corresponds to a conservative substitution technique. In addition, the following substitutions also correspond to conservative substitutions: substitutions between amino acid residues having acidic side chains, such as aspartic acid and glutamic acid; substitutions between amino acid residues having uncharged polar side chains, such as glycine, asparagine, glutamine, serine, threonine, tyrosine, and cysteine; substitutions between amino acid residues having nonpolar side chains, such as alanine, valine, leucine, isoleucine, proline, phenylalanine, methionine, and tryptophan; substitutions between amino acid residues having β-branched side chains, such as threonine, valine, and isoleucine; and substitutions between amino acid residues having aromatic side chains, such as tyrosine, phenylalanine, tryptophan, and histidine.

In the protein set forth in (b) above, when amino acid(s) are substituted, deleted, added, or inserted in the amino acid sequence set forth in SEQ ID NO: 1 or 2, it is desirable that amino acid(s) be substituted, deleted, added, or inserted at site(s) that do not impair the function of ANGPTL7 as a ligand.

ANGPTL7 may be chemically modified as long as it has an action of promoting corneal tissue repair and/or an action of promoting neurite formation of the ophthalmic nerve.

In ANGPTL7, the C-terminus may be a carboxyl group (—COOH), a carboxylate (—COO⁻), an amide (—CONH$_2$), or an ester (—COOR).

The group represented by R in the ester may be, for example, a $C_{1-6}$ alkyl group, such as methyl, ethyl, n-propyl, isopropyl, or n-butyl; a $C_{3-8}$ cycloalkyl group, such as cyclopentyl or cyclohexyl; a $C_{6-12}$ aryl group, such as phenyl or α-naphthyl; a phenyl-$C_{1-2}$ alkyl group, such as benzyl or phenethyl; a $C_{7-14}$ aralkyl group, such as an α-naphthyl-$C_{1-2}$ alkyl group, for example, α-naphthylmethyl; a pivaloyloxymethyl group; or the like.

In ANGPTL7, a carboxyl group (or carboxylate) at a position other than the C-terminus may be amidated or esterified. Examples of the ester in this case include the above-mentioned C-terminal esters.

Further, ANGPTL7 includes those wherein the amino group of the N-terminal amino acid residue is protected by a protecting group (e.g., a $C_{1-6}$ acyl group such as $C_{1-6}$ alkanoyl, such as formyl or acetyl); those wherein the N-terminal glutamine residue that can be produced by cleavage in vivo is converted to pyroglutamic acid; those wherein a substituent (e.g., —OH, —SH, an amino group, an imidazole group, an indole group, or guanidino group) on the side chain of an amino acid in the molecule is protected by an appropriate protecting group (e.g., a $C_{1-6}$ acyl group such as $C_{1-6}$ alkanoyl, such as formyl or acetyl); conjugated proteins such as those called glycoproteins having sugar chains bound thereto; and the like.

ANGPTL7 may be one with a known protein tag added thereto as long as it has an action of promoting corneal tissue repair and/or an action of promoting neurite formation of the ophthalmic nerve. Examples of protein tags include histidine tags, FLAG tags, GST tags, and the like.

ANGPTL7 may be in the form of a pharmaceutically acceptable salt with an acid or a base. The salt is not particularly limited as long as it is pharmaceutically acceptable, and may be an acid salt or a basic salt. Examples of acid salts include inorganic acid salts, such as hydrochloride, hydrobromide, sulfate, nitrate, and phosphate; organic acid salts, such as acetate, propionate, tartrate, fumarate, maleate, malate, citrate, methanesulfonate, and paratoluenesulfonate; amino acid salts, such as aspartate and glutamate; and the like. Examples of basic salts include alkali metal salts, such as sodium salts and potassium salts; alkaline earth metal salts, such as calcium salts and magnesium salts; and the like.

ANGPTL7 may be in the form of a solvate. The solvent is not particularly limited as long as it is pharmaceutically acceptable. Examples of solvents include water, ethanol, glycerol, acetic acid, and the like.

ANGPTL7 can be obtained according to a known method, such as chemical synthesis, purification from mammalian cells or tissue (such as ocular tissue), or purification from a transformant containing a polynucleotide encoding ANGPTL7. When ANGPTL7 is obtained by purification from a transformant, the transformant is not particularly limited as long as it is a cell capable of expressing ANGPTL7 from a polynucleotide encoding ANGPTL7, and various cells, such as bacteria including Escherichia coli, insect cells, and mammalian cells can be used.

Since ANGPTL7 is believed to be present as a glycoprotein having sugar chain(s) bound thereto in vivo, the transformant is preferably a cell in which sugar chain modification is performed, specifically, an insect cell, an animal cell, or the like, from the standpoint of obtaining ANGPTL7 in a state closer to that in vivo.

Examples of usable insect cells include Sf cells, MG1 cells, High Five™ cells, BmN cells, and the like. Examples of usable Sf cells include Sf9 cells (ATCC CRL1711), Sf21 cells, and the like.

Examples of usable animal cells include monkey COS-7 cells, monkey Vero cells, Chinese hamster cells CHO, mouse L cells, mouse AtT-20 cells, mouse myeloma cells, rat GH3 cells, human FL cells, and the like.

The agent of the present invention may consist of ANGPTL7 or may be a composition comprising ANGPTL7 and optionally comprising one or more pharmaceutically acceptable additives (which may be simply referred to herein as "additives").

Examples of the subject of administration of the agent of the present invention include mammals (e.g., human, mouse, rat, hamster, rabbit, cat, dog, bovine, sheep, monkey, etc.).

The administration route of the agent of the present invention is not particularly limited. Examples include enteral administration, such as oral administration, tube feeding, and enema administration; parenteral administration, such as intravenous administration, intra-arterial administration, intramuscular administration, intracardiac administration, subcutaneous administration, intradermal administration, intraperitoneal administration, and ocular topical administration (instillation administration, intravitreal administration, subconjunctival administration, sub-tenon administration, etc.); and the like. Among these, for example, parenteral administration is preferable, and ocular topical administration is more preferable, from the standpoint of exhibiting the effects of the present invention more reliably.

The agent of the present invention can take a dosage form suitable for the administration route. Examples of dosage forms suitable for oral administration include tablets, capsules, granules, powders, and the like. Examples of dosage forms suitable for parenteral administration include ophthalmic compositions (agents that are topically applied to the eye: eye drops, ophthalmic ointments, eye washes, etc.), injections, patches, lotions, creams, and the like. These can be prepared using an ordinary technique widely used in the art. In addition, ANGPTL7 can also be formulated into, in addition to the above preparations, preparations for intraocular implants and preparations designed for DDS (drug delivery systems), such as microsphere.

Examples of additives include bases, carriers, solvents, dispersing agents, emulsifiers, buffers, stabilizers, excipients, binders, disintegrators, lubricants, thickeners, humectants, coloring agents, flavors, chelating agents, and the like. These may be suitably selected according to the administration route, dosage form, etc.

For example, when ophthalmic compositions (agents that are topically applied to the eye: eye drops, ophthalmic ointments, eye washes, or the like) comprising ANGPTL7 as an active ingredient are prepared, stabilizers (such as sodium hydrogen sulfite, sodium thiosulfate, sodium edetate, sodium citrate, ascorbic acid, and dibutylhydroxytoluene), solubilizing agents (such as glycerin, propylene glycol, macrogol, and polyoxyethylene hydrogenated castor oil), suspending agents (such as polyvinylpyrrolidone, hydroxypropylmethylcellulose, hydroxymethylcellulose, and sodium carboxymethylcellulose), emulsifiers (such as polyvinylpyrrolidone, soybean lecithin, egg yolk lecithin, polyoxyethylene hydrogenated castor oil, and polysorbate 80), buffers (such as phosphate buffer, acetate buffer, borate buffer, carbonate buffer, citrate buffer, tris buffer, glutamic acid, and epsilon-aminocaproic acid), thickeners (such as methylcellulose, hydroxyethylcellulose, hydroxypropylmethylcellulose, carboxymethylcellulose, and like water-soluble cellulose derivatives, sodium chondroitin sulfate, sodium hyaluronate, carboxyvinyl polymer, polyvinyl alcohol, polyvinylpyrrolidone, and macrogol), preservatives (such as benzalkonium chloride, benzethonium chloride, chlorhexidine gluconate, chlorobutanol, benzyl alcohol, sodium dehydroacetate, p-hydroxybenzoates, sodium edetate, and boric acid), isotonizing agents (such as sodium chloride, potassium chloride, glycerin, mannitol, sorbitol, boric acid, glucose, and propylene glycol), pH adjusters (such as hydrochloric acid, sodium hydroxide, phosphoric acid, and acetic acid), cooling agents (such as l-menthol, d-camphor, d-borneol, and peppermint oil), ointment bases (such as white petrolatum, purified lanolin, liquid paraffin, vegetable oil (olive oil, camellia oil, peanut oil, etc.)), and the like can be added as additives. The amounts of these additives added vary depending on the kind, use, etc., of the additives added, and they may be added at concentrations capable of achieving the object of the additives.

When the agent of the present invention is provided in the form of an ophthalmic composition, such as eye drops or an ophthalmic ointment, the agent can be produced according to a method generally used in the pharmaceutical field, for example, based on the method described in the section on eye drops or the section on ophthalmic ointments in General Rules for Preparation of the Japanese Pharmacopoeia, 15th Edition.

The dosage of the agent of the present invention varies depending on the target disease, and cannot be generalized; however, it can be set such that the concentration of ANGPTL7 in the target tissue where the desired effect is to be exhibited is, for example, 0.001 nM to 100 μM, and preferably 0.01 nM to 100 μM.

When the agent of the present invention is topically used for adult eyes, it is recommended that an ophthalmic composition containing ANGPTL7 in an amount of, for example, 0.01 nM to 1000 μM, and preferably 0.1 nM to 1000 μM, be applied 1 to 8 times, and preferably 1 to 5 times, a day. The amount of the composition applied can be suitably set according to the concentration of ANGPTL7 and the dosage form.

ANGPTL7 is useful for preventing or treating a corneal disorder.

The corneal disorder refers to a disease in which corneal tissue is damaged by various factors.

The corneal disorder is preferably, for example, corneal epithelial disorder, dry eye, or reduction in corneal sensitivity.

The corneal epithelial disorder refers to a disease developed by an imbalance of epithelial homeostasis when the corneal epithelial cell proliferation ability is suppressed or epithelial shedding is promoted. The corneal epithelial disorder also means that the corneal epithelium is damaged by an endogenous disease, such as a corneal ulcer, corneal epithelial abrasion, diabetic keratopathy, keratoconjunctivitis sicca, chronic superficial keratitis, superficial punctate keratopathy, corneal erosion, or persistent corneal epithelial defect, by an exogenous disease caused by, for example, a drug, injury, or wearing contact lenses, or by physical or chemical injury.

Dry eye is a chronic disease of tears and the keratoconjunctival epithelium due to various causes, accompanied by eye discomfort and visual dysfunction. Tear abnormalities include quantitative abnormalities, in which the amount of tears decreases, and qualitative abnormalities, in which the properties of tears or the ability to retain tears changes. Examples of dry eye include lacrimal hyposecretion; evaporative dry eye; Sjögren's syndrome; Stevens-Johnson syndrome; dry eye associated with corneal epithelial erosion, marginal blepharitis, ocular pemphigoid, vernal keratoconjunctivitis, allergic conjunctivitis, vitamin A deficiency, or the like; and the like.

Examples of reduction in corneal sensitivity include reduction in corneal sensitivity associated with diseases, such as corneal epithelial disorder, dry eye, neuroparalytic keratopathy, corneal ulcer, neurotrophic keratopathy, diabetic keratopathy, keratoconjunctivitis (epidemic keratoconjunctivitis, herpes simplex keratitis), keratoconus, and corneal degeneration; and reduction in corneal sensitivity associated with cataract surgery, vitreous surgery, or corneal surgery, such as PRK, LASIK, LASEK, or corneal transplantation surgery. Corneal reduction in corneal sensitivity and improvement thereof can be measured by a usual method using an aesthesiometer, such as a Cochet-Bonnet aesthesiometer.

It is known that, in dry eye patients, lacrimal hypofunction causes reduction in corneal sensitivity and that reduction in corneal sensitivity leads to further lacrimal hypofunction. It has been reported that this vicious circle aggravates dry eye symptoms, and even causes corneal epithelial disorder. For example, a paper by Mathers (CLAO J. 2000, 26, 159.) reports a "corneal lacrimal gland feedback model" in which the lacrimal glands and cornea are tightly integrated in the onset of disease, lacrimal gland disease influences the ocular surface, and ocular surface disease influences the lacrimal glands. Mathers shows that reduction in corneal sensitivity induces lacrimal hyposecretion and then leads to corneal epithelial disorder, resulting in lacrimal gland disorder, and that these occur in a vicious circle (in particular, page 161, right column, lines 39 to 45). A paper by Ang et al. (Curr Opin Ophthalmol. 2001, 12, 318.) indicates that a primary cause of corneal epithelial disorder, such as superficial punctate keratopathy, is reduction in corneal sensitivity, which results in decreased feedback to the lacrimal glands and reduced tear production. A paper by Xu et al. (Cornea 1996, 15, 235.) states that decreased formation of tears may lead to morphological changes in the corneal epithelium and reduction in corneal sensitivity (for example, page 238, right column, lines 44 to 47). A paper by Fujishima et al. (Cornea 1996, 15, 368.) suggests that, in a study using an aldose reductase inhibitor, an improvement in the dynamics of tear production may be due to an improvement in corneal sensitivity. It is thus believed that corneal epithelial disorder, dry eye, and reduction in corneal sensitivity are closely related and that each causes the other diseases. ANGPTL7 enables both corneal tissue repair and improvement in reduction in corneal sensitivity based on the action of promoting corneal tissue repair and/or the action of promoting neurite formation of the ophthalmic nerve, and thus can be expected to prevent or treat the above diseases efficiently.

"Corneal tissue repair" refers to effecting improvement, preferably the cure of a corneal disorder.

"neurite formation of the ophthalmic nerve" refers to the formation and/or extension of a projection (dendrite and axon) from the cell body of an ophthalmic nerve cell.

The corneal tissue is not particularly limited as long as it is tissue in the cornea, and preferable examples of the corneal tissue are the corneal epithelium and corneal nerves (which may be referred to herein as "trigeminal nerve"). The ophthalmic nerve is not limited as long as it is a nerve present in ocular tissue, and examples include various nerves, such as corneal nerves, retinal nerves, the oculomotor nerve, and the ciliary ganglion. Among these, for example, corneal nerves are preferable.

"Corneal nerves" refer to annular plexus formed in the surrounding cornea, stromal plexus distributed reticulately in the corneal stroma, sub-epithelial plexus formed immediately below the Bowman's membrane, and subbasal plexus and nerve fiber formed immediately after penetrating the Bowman's membrane, under the control of the trigeminal nerve, which is a sensory nerve.

EXAMPLES

Examples are given below to illustrate the present invention in more detail, but the present invention is not limited to these Examples.

Test Example 1: Effect of ANGPTL7 on Corneal Tissue Repair After Corneal Injury 1-1. Animals Used Male C57BL/6 mice with a body weight of about 20 g were used. They were bred at a temperature of 24±4° C. and a humidity of 55±15%.

1-2. Test Reagent

Recombinant angiopoietin-like protein 7 from mice (R&D Systems, 4960-AN-025/CF) (hereinafter, referred to as "rmANGPTL7") was used.

1-3. Test Method

The mice were divided into an rmANGPTL7 administration group (5 eyes) and a control (PBS administration) group (4 eyes). Each mouse underwent general anesthesia by intramuscular injection of a mixture of equal amounts of 5% ketamine and 2% xylazine and local anesthesia by instillation of oxybuprocaine hydrochloride. Immediately after 5 µL of 70% ethanol was applied to the cornea dropwise, the corneal epithelium was abraded by blunt dissection with a spatula. Fluorescein staining was performed, followed by observation with a slit lamp immediately after the abrasion of the corneal epithelium and 24 hours after the abrasion of the corneal epithelium. The test reagent was administered by subconjunctival injection immediately after the abrasion of the corneal epithelium (5 µL of the reagent dissolved to a concentration of 500 µg/mL in PBS was administered under each of the upper and lower conjunctivae). To the control group, physiological saline was administered subconjunctivally in a similar manner.

1-4. Test Results

The upper portion of FIG. 1 shows images obtained by observation immediately after the abrasion of the corneal epithelium, and the lower portion of FIG. 1 shows images obtained by observation 24 hours after the abrasion of the corneal epithelium. The left side of FIG. 1 shows images of the control group obtained by observation, and the right side of FIG. 1 shows images of the test reagent (ANGPTL7) administration group obtained by observation. In the images obtained by observation, yellow, greenish yellow, and green portions indicate portions where the corneal epithelium was abraded, and blue portions indicate portions where the corneal epithelium was not abraded or the corneal epithelium was repaired after the abrasion of the corneal epithelium.

Immediately after the abrasion of the corneal epithelium, the corneal epithelium was abraded throughout the cornea (upper portion of FIG. 1), whereas 24 hours after the abrasion of the corneal epithelium, the corneal epithelium was repaired in both of the control group and the test reagent administration group; however, the area of the repaired portions (blue portions) was larger in the test reagent administration group (lower portion of FIG. 1).

The above results revealed that ANGPTL7 has an action of promoting corneal tissue repair.

Test Example 2: Effect of ANGPTL7 on Corneal Nerve Repair (the Central Portion of the Cornea) After Corneal Injury 2-1. Animals Used Male C57BL/6 mice with a body weight of about 20 g were used. They were bred at a temperature of 24±4° C. and a humidity of 55±15%.

2-2. Test Reagent

Recombinant ANGPTL7 from mice (R&D Systems, 4960-AN-025/CF) (hereinafter, referred to as "rmANGPTL7") was used.

2-3. Test Method

The corneal epithelium was abraded in a manner similar to that in Test Example 1, and the test reagent was administered by subconjunctival injection immediately after the abrasion of the corneal epithelium (5 µL of the reagent dissolved to a concentration of 500 µg/mL in PBS was administered under each of the upper and lower conjunctivae). To the control group, physiological saline was administered subconjunctivally in a similar manner. The mice were euthanized by cervical dislocation 5 days after the abrasion of the corneal epithelium, and the eyeballs were removed. The eyeballs were immersed in Zamboni fixative and rotated at room temperature for 10 to 15 minutes, and the Zamboni fixative was replaced with physiological saline. As shown in the upper portion of FIG. 2, each eyeball was divided in half at the equator portion, the anterior segment of the eye including the cornea was collected, and the lens and the iris were removed. After the tissue samples were immersed in Zamboni fixative again and rotated at room temperature for 45 minutes for further fixation, the Zamboni fixative was replaced with PBS.

Immunostaining was performed using an anti-β3 tubulin antibody. The fixed tissue samples were blocked in a blocking buffer (PBS containing 5% normal goat serum, 2% skim milk, and 0.5% Triton-X100) at room temperature for 2 hours. A primary antibody (anti-β3 tubulin antibody, ab18207, Abcam) was diluted 1:500 with a blocking buffer, and the tissue samples were allowed to react in this primary antibody dilution at 4° C. overnight. After the reaction with the primary antibody, the tissue samples were washed with PBS containing 0.5% Triton-X100 (90 minutes×three times). A secondary antibody (Alexa Fluoro 488 goat anti-rabbit IgG, A11034, Life Technologies Corporation) was diluted 1:200 with a blocking buffer, and the tissue samples were allowed to react in this secondary antibody dilution at room temperature for 2 hours. After the reaction with the secondary antibody, the tissue samples were washed with PBS containing 0.5% Triton-X100 (90 minutes×three times) and further washed with PBS (45 minutes×three times). Each tissue sample was adhered to a slide glass and mounted with an antifading agent (VectaShield, Vector Laboratories), followed by observation under confocal microscope (Carl Zeiss). The stained cells were imported as images from the confocal microscope into a computer. As shown in the upper portion of FIG. 2, the observation was performed at four sites in the region from the center of the cornea to the middle of the cornea (region A).

2-4. Test Results

Figure 2:
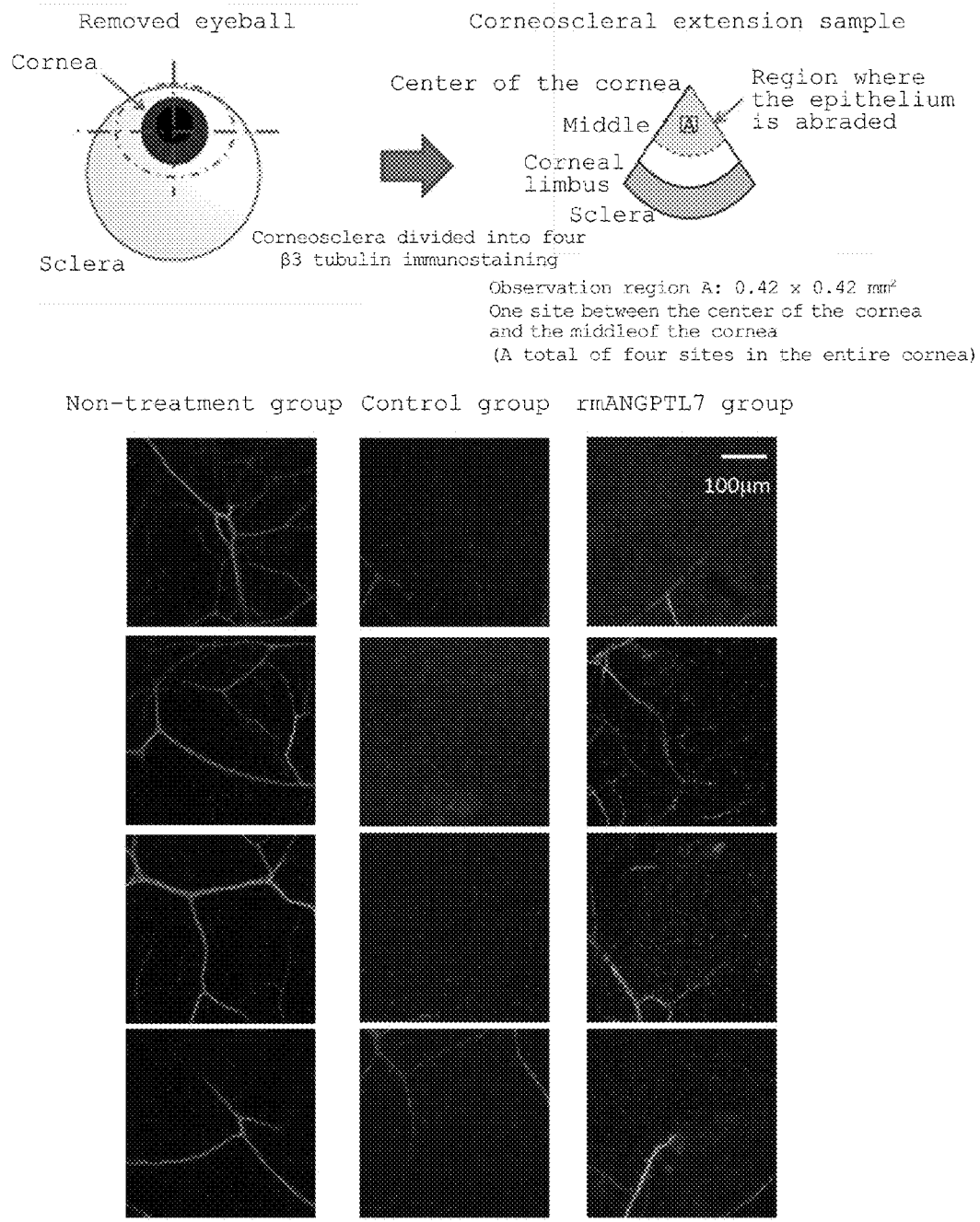
FIG. 2 is a summary view of Test Example 2 (upper portion).

The results of the observation are shown in the lower portion of FIG. 2. In FIG. 2, the images in the non-treatment group are immunostaining images of the cornea whose corneal epithelium was not abraded. As shown in the lower portion of FIG. 2, nerve fibers were observed in region A in both the control group and the rmANGPTL7 administration group; however, the number of fibers was clearly larger in the rmANGPTL7 administration group.

The above results revealed that ANGPTL7 has an action of promoting corneal nerve repair.

Test Example 3: Effect of ANGPTL7 on Corneal Nerve Repair (the Peripheral Portion of the Cornea) after Corneal Injury 3-1. Animals Used Male C57BL/6 mice with a body weight of about 20 g were used. They were bred at a temperature of 24±4° C. and a humidity of 55±15%.

3-2. Test Reagent

Recombinant ANGPTL7 from mice (R&D Systems, 4960-AN-025/CF) (hereinafter referred to as "rmANGPTL7") was used.

3-3. Test Method

The corneal epithelium was abraded in a manner similar to that in Test Example 1, and the test reagent was administered by subconjunctival injection immediately after the abrasion of the corneal epithelium (5 μL of the reagent dissolved to a concentration of 500 μg/mL in PBS was administered under each of the upper and lower conjunctivae). To the control group, physiological saline was administered subconjunctivally in a similar manner. The mice were euthanized by cervical dislocation 5 days after the abrasion of the corneal epithelium, and the eyeballs were removed. The eyeballs were immersed in Zamboni fixative and rotated at room temperature for 10 to 15 minutes, and the Zamboni fixative was replaced with physiological saline. As shown in the upper portion of FIG. 3, each eyeball was divided in half at the equator portion, the anterior segment of the eye including the cornea was collected, and the lens and the iris were removed. After the tissue samples were immersed in Zamboni fixative again and rotated at room temperature for 45 minutes for further fixation, the Zamboni fixative was replaced with PBS.

Figure 3:
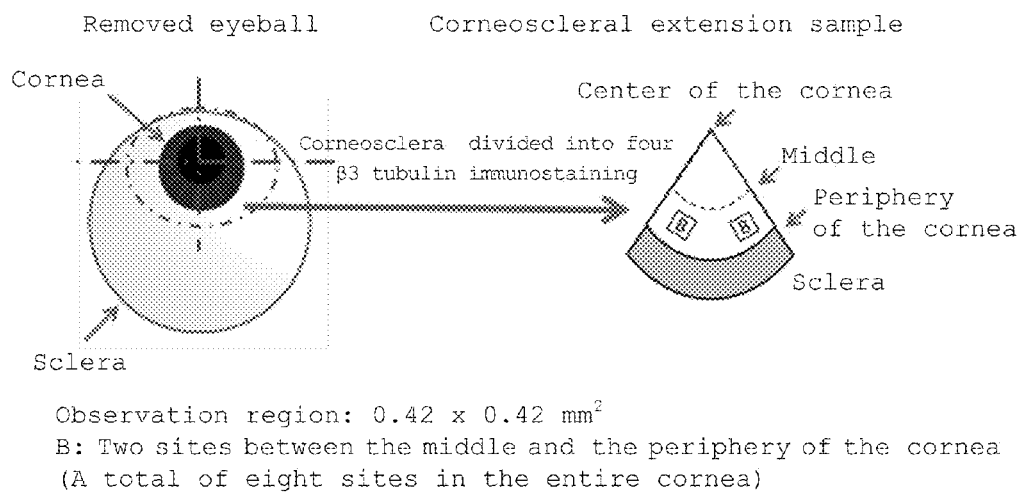
FIG. 3 is a summary view of Test Example 3 (Test Example 3).

Immunostaining was performed using an anti-β3 tubulin antibody. The fixed tissue samples were blocked in a blocking buffer (PBS containing 5% normal goat serum, 2% skim milk, and 0.5% Triton-X100) at room temperature for 2 hours. A primary antibody (anti-β3 tubulin antibody, ab18207, Abcam) was diluted 1:500 with a blocking buffer, and the tissue samples were allowed to react in this primary antibody dilution at 4° C. overnight. After the reaction with the primary antibody, the tissue samples were washed with PBS containing 0.5% Triton-X100 (90 minutes×three times). A secondary antibody (Alexa Fluoro 488 goat anti-rabbit IgG, A11034, Life Technologies Corporation) was diluted 1:200 with a blocking buffer, and the tissue samples were allowed to react in this secondary antibody dilution at room temperature for 2 hours. After the reaction with the secondary antibody, the tissue samples were washed with PBS containing 0.5% Triton-X100 (90 minutes×three times) and further washed with PBS (45 minutes×three times). Each tissue sample was adhered to a slide glass and mounted with an antifading agent (VectaShield, Vector Laboratories), followed by observation under confocal microscope (Carl Zeiss). The stained cells were imported as images from the confocal microscope into a computer. As shown in FIG. 3, the observation was performed at eight sites in the region from the center of the cornea to the middle of the cornea (region B).

Comparing the nerve fibers in the rmANGPTL7 administration group with those in the control group, when the number of nerve fibers in the rmANGPTL7 administration group is larger than that in the control group, ANGPTL7 can be confirmed to have an action of promoting corneal nerve repair.

Test Example 4: Effect of ANGPTL7 on Neurite Formation in Trigeminal Nerve Cells 4-1. Animals Used SD juvenile rats (7 days old, male and female) purchased from Japan SLC, Inc. were used.

4-2. Test reagent

Recombinant angiopoietin-like protein 7 from mice (R&D Systems, 4960-AN-025/CF; hereinafter referred to as "rmANGPTL7") was used.

4-3. Test Method 4-3-1. Cell Culture

Rat trigeminal nerve cells were isolated according to the report of Chan et al. (Kwan Y. Chan and Richard H. Haschke. Exp. Eye Res. 41: 687-699, 1985). More specifically, after each rat was euthanized by carbon dioxide gas, the trigeminal ganglion was cut out from the rat. The trigeminal ganglion cut out was washed with Hanks' balanced salt solution (HBSS, Invitrogen), cut into small pieces in a 3 mg/mL collagenase A (Roche) solution with scissors, and then treated in the solution at 37° C. for 30 minutes. After the treatment, centrifugation was performed at 120×g for 5 minutes, and the supernatant was removed. The enzyme liquid of Nerve Cell Dissociation Medium Set (DS Pharma Biomedical Co., Ltd.) was added to the precipitate, followed by treatment at 37° C. for 40 minutes. After the treatment, centrifugation was performed at 120×g for 5 minutes, and the supernatant was removed. Thereafter, treatment was conducted with dispersion liquid and an isolation liquid according to the protocol attached to the Nerve Cell Dissociation Medium Set. After the treatment, centrifugation was performed at 120×g for 5 minutes, and the supernatant was removed, followed by resuspension in 3 mL of 9.3% BSA solution. The suspension was centrifuged at 120×g at room temperature for 30 minutes, and the supernatant was removed, followed by resuspension in 2 mL of culture medium. The number of cells in the suspension was counted, and the cells were seeded on an 8-well chamber slide (Becton, Dickinson and Company) coated with polylysine/laminin at about $2.5 \times 10^3$ cells/well. At the same time, each of rmANGPTL7 (final concentration: 0.1 nM, 1 nM, or 10 nM), Glial-Derived Neurotrophic Factor (GDNF) (final concentration: 0.1 nM) as a positive control, and PBS as a control was individually added to the culture medium, and then the cells were cultured for 24 hours.

The culture medium used was Neurobasal Medium containing B27 supplement (Life Technologies Japan Ltd.) (final concentration: 2% (v/v)) and L-glutamine (Life Technologies Japan Ltd.) (final concentration: 1 mM). The culture conditions were as follows: a carbon dioxide concentration of 5%, an air concentration of 95%, a humidity of 100%, and a temperature of 37° C.

4-3-2. Staining

After the 24 hours of culture following the seeding, the rat trigeminal nerve cells were immersed and fixed in 10% neutral buffered formaldehyde liquid at room temperature for 20 minutes. Double staining was performed using anti-neurofilament 200 antibody (MAB5446, Millipore), which specifically recognizes neurofilaments constituting cell bodies of Aα•Aβ•Aδ of the trigeminal nerve and neurites, and anti-substance P antibody (20064, Immunostar), which recognizes cell bodies of Aδ•c of trigeminal nerve cells, to allow detection of cell bodies of Aδ, which is a corneal sensory nerve contributing to physical stimulation. A fluorescence-labeled secondary antibody was allowed to react, followed by observation under a fluorescence microscope (Olympus Corporation). The stained cells were imported as images from the fluorescence microscope to a computer.

4-3-3. Image Analysis

To evaluate the degree of neurite formation in the cultured rat trigeminal nerve cells, cell body diameters and neurite lengths were measured on the computer-captured stained cell images using image analysis software (ImageJ Ver. 1.47, National Institutes of Health). Cells having a neurite with a length of not less than twice the diameter of the cell body were regarded as neurite formation cells, and the percentage (%) of the cells in the total number of cells was calculated (Otori Y, Wei J Y, Barnstable C J. Invest. Ophthalmol Vis Sci (1998) 39, 972-981).

4-3-4. Statistical Analysis

Statistical processing was performed using JMP (Ver. 10.02, SAS Institute Japan) by Dunnett's test of multiple comparisons to the control group. A p value of 0.05 or less was determined as significant.

4-4. Test Results

Figure 4:
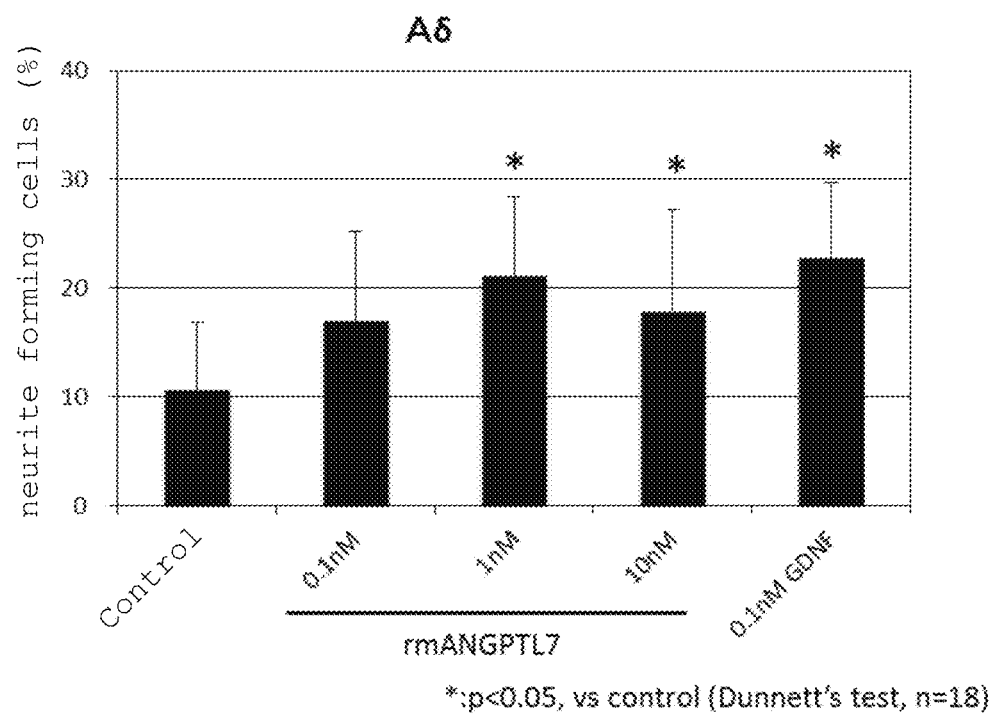
FIG. 4 shows the proportion (%) of neurite forming cells in the total number of Aδ cells (Test Example 4). In the graph, * indicates a significant difference from the control group (p<0.05).
Figure 5:
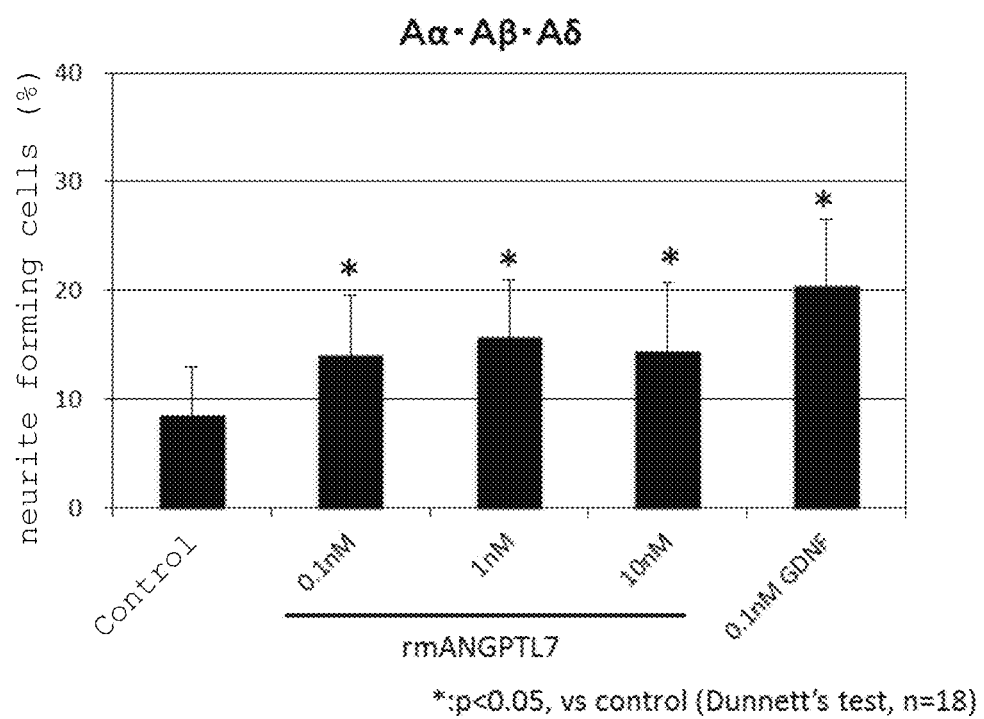
FIG. 5 shows the proportion (%) of neurite forming cells in the total number of Aα•Aβ•Aδ cells (Test Example 4). In the graph, * indicates a significant difference from the control group (p<0.05).
Figure 6:
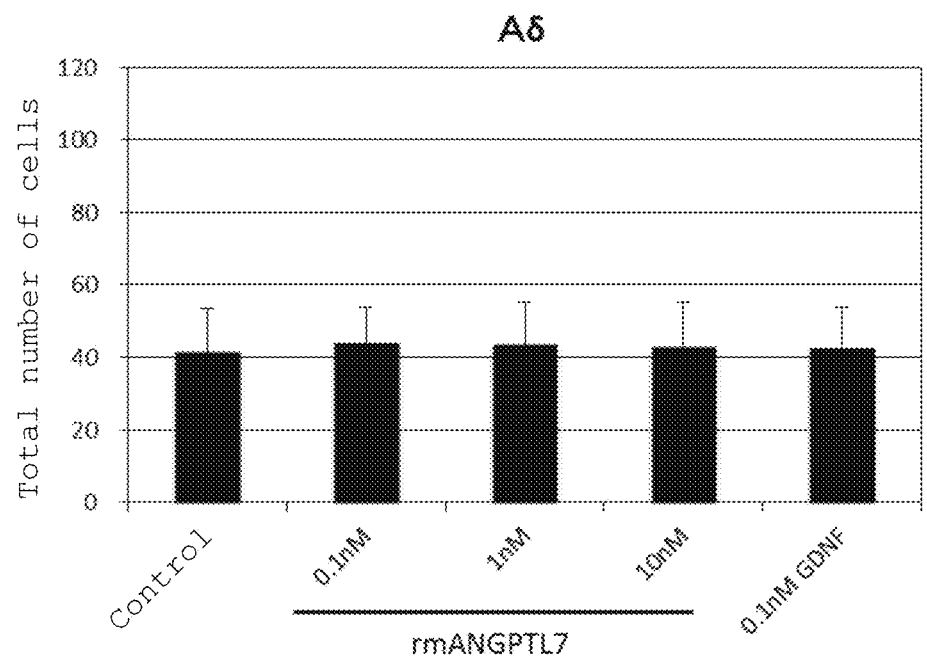
FIG. 6 shows the total number of Aδ cells (Test Example 4).
Figure 7:
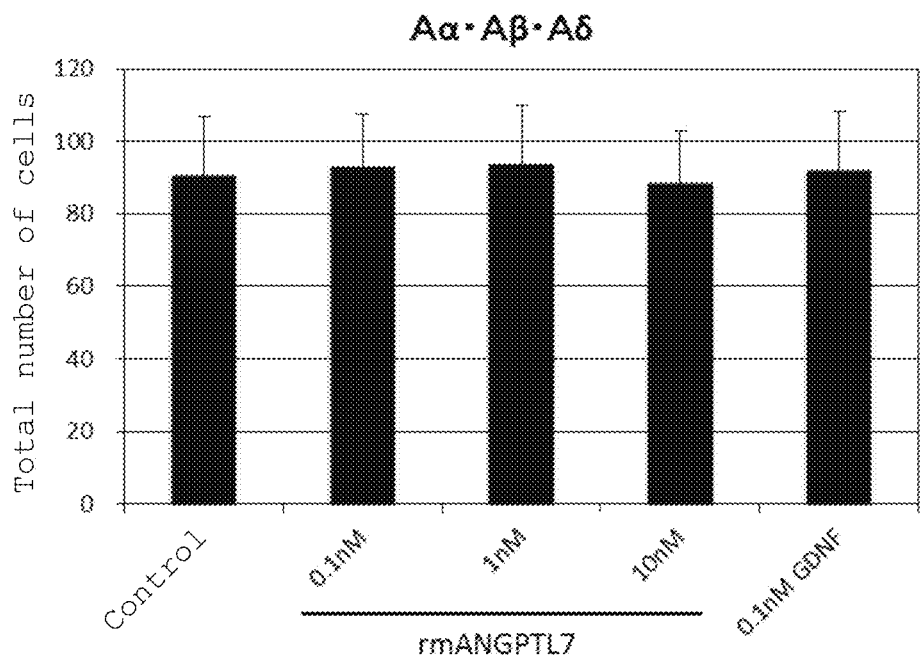
FIG. 7 shows the total number of Aα•Aβ•Aδ cells (Test Example 4).

FIGS. 4 and 5 are graphs showing the percentage (%) of neurite formation cells in the total number of cells. FIGS. 6 and 7 are graphs showing the number of counted cells. FIGS. 4 and 6 show the results of counting of only Aδ cells, and FIGS. 5 and 7 show the results of counting Aα•Aβ•Aδ cells.

In the group to which 0.1 nM GDNF was added as a positive control, the percentage of neurite formation cells was significantly higher than that in the control group both when only Aδ cells were counted and when Aα•Aβ•Aδ cells were counted (FIGS. 4 and 5). In the group to which 1 nM or 10 nM rmANGPTL7 was added, the percentage of neurite formation cells was significantly higher than that in the control group both when only Aδ cells were counted and when Aα•Aβ•Aδ cells were counted (FIGS. 4 and 5). In the group to which 0.1 nM rmANGPTL7 was added, the percentage of neurite formation cells was significantly higher than that in the control group when Aα•Aβ•Aδ cells were counted, and the percentage of neurite formation cells also tended to be higher than that in the control group when only Aδ cells were counted (FIGS. 4 and 5). There was no significant difference in the total number of counted cells between the groups both when only Aδ cells were counted and when Aα•Aβ•Aδ cells were counted. This suggests that the differences in the percentage of neurite formation cells between the groups were not attributed to changes in the number of cells (FIGS. 6 and 7).

The above results revealed that ANGPTL7 has an action of promoting neurite formation of trigeminal nerve cells.

The invention claimed is:

1. A method for treating a corneal disorder selected from one or more of an endogenous corneal epithelial disorder, dry eye, and reduction in corneal sensitivity, comprising administering angiopoietin-like protein 7 to a patient in need thereof.

2. The method according to claim 1, wherein the corneal disorder is endogenous corneal epithelial disorder.

3. A method for promoting corneal tissue repair in a patient in need of treatment for one or more of an endogenous corneal epithelial disorder, dry eye, and reduction in corneal sensitivity, comprising administering angiopoietin-like protein 7 to the patient.

4. The method according to claim 3, wherein the corneal tissue is one or more selected from corneal epithelium and corneal nerves.

5. A method for promoting neurite formation of an ophthalmic nerve in a patient in need of treatment for one or more of an endogenous corneal epithelial disorder, dry eye, and reduction in corneal sensitivity, comprising administering angiopoietin-like protein 7 to the patient.

6. The method according to claim 5, wherein the ophthalmic nerve is corneal nerves.

7. The method according to claim 1, wherein the subject is a mammal.

8. The method according to claim 1, wherein the subject is a human.

9. The method according to claim 1, wherein the administering comprises topically administering an ophthalmic composition comprising the angiopoietin-like protein 7 to the subject's eye(s).

10. The method according to claim 3, wherein the subject is a mammal.

11. The method according to claim 3, wherein the subject is a human.

12. The method according to claim 3, wherein the administering comprises topically administering an ophthalmic composition comprising the angiopoietin-like protein 7 to the subject's eye(s).

13. The method according to claim 5, wherein the subject is a mammal.

14. The method according to claim 5, wherein the subject is a human.

15. The method according to claim 5, wherein the administering comprises topically administering an ophthalmic composition comprising the angiopoietin-like protein 7 to the subject's eye(s).

16. The method according to claim 1, wherein the corneal disorder is dry eye.

17. The method according to claim 1, wherein the corneal disorder is reduction in corneal sensitivity.

* * * * *

SEQUENCE LISTING

```
<160> NUMBER OF SEQ ID NOS: 2

<210> SEQ ID NO 1
<211> LENGTH: 346
<212> TYPE: PRT
<213> ORGANISM: Homo sapiens

<400> SEQUENCE: 1

Met Leu Lys Lys Pro Leu Ser Ala Val Thr Trp Leu Cys Ile Phe Ile
1               5                   10                  15

Val Ala Phe Val Ser His Pro Ala Trp Leu Gln Lys Leu Ser Lys His
            20                  25                  30

Lys Thr Pro Ala Gln Pro Gln Leu Lys Ala Ala Asn Cys Cys Glu Glu
        35                  40                  45

Val Lys Glu Leu Lys Ala Gln Val Ala Asn Leu Ser Ser Leu Leu Ser
    50                  55                  60

Glu Leu Asn Lys Lys Gln Glu Arg Asp Trp Val Ser Val Val Met Gln
65                  70                  75                  80
```

```
Val Met Glu Leu Glu Ser Asn Ser Lys Arg Met Glu Ser Arg Leu Thr
                85                  90                  95

Asp Ala Glu Ser Lys Tyr Ser Glu Met Asn Asn Gln Ile Asp Ile Met
            100                 105                 110

Gln Leu Gln Ala Ala Gln Thr Val Thr Gln Thr Ser Ala Asp Ala Ile
        115                 120                 125

Tyr Asp Cys Ser Ser Leu Tyr Gln Lys Asn Tyr Arg Ile Ser Gly Val
    130                 135                 140

Tyr Lys Leu Pro Pro Asp Asp Phe Leu Gly Ser Pro Glu Leu Glu Val
145                 150                 155                 160

Phe Cys Asp Met Glu Thr Ser Gly Gly Gly Trp Thr Ile Ile Gln Arg
                165                 170                 175

Arg Lys Ser Gly Leu Val Ser Phe Tyr Arg Asp Trp Lys Gln Tyr Lys
            180                 185                 190

Gln Gly Phe Gly Ser Ile Arg Gly Asp Phe Trp Leu Gly Asn Glu His
        195                 200                 205

Ile His Arg Leu Ser Arg Gln Pro Thr Arg Leu Arg Val Glu Met Glu
    210                 215                 220

Asp Trp Glu Gly Asn Leu Arg Tyr Ala Glu Tyr Ser His Phe Val Leu
225                 230                 235                 240

Gly Asn Glu Leu Asn Ser Tyr Arg Leu Phe Leu Gly Asn Tyr Thr Gly
                245                 250                 255

Asn Val Gly Asn Asp Ala Leu Gln Tyr His Asn Asn Thr Ala Phe Ser
            260                 265                 270

Thr Lys Asp Lys Asp Asn Asp Asn Cys Leu Asp Lys Cys Ala Gln Leu
        275                 280                 285

Arg Lys Gly Gly Tyr Trp Tyr Asn Cys Cys Thr Asp Ser Asn Leu Asn
    290                 295                 300

Gly Val Tyr Tyr Arg Leu Gly Glu His Asn Lys His Leu Asp Gly Ile
305                 310                 315                 320

Thr Trp Tyr Gly Trp His Gly Ser Thr Tyr Ser Leu Lys Arg Val Glu
                325                 330                 335

Met Lys Ile Arg Pro Glu Asp Phe Lys Pro
            340                 345

<210> SEQ ID NO 2
<211> LENGTH: 337
<212> TYPE: PRT
<213> ORGANISM: Mus musculus

<400> SEQUENCE: 2

Met Leu Arg Glu Thr Trp Leu Cys Val Ile Leu Val Ala Phe Val Ser
1               5                   10                  15

His Pro Val Trp Leu Gln Lys Pro His Lys Arg Lys Thr Gln Leu Lys
                20                  25                  30

Ala Ala Gly Cys Cys Glu Glu Met Arg Glu Leu Lys Ala Gln Val Ala
            35                  40                  45

Asn Leu Ser Ser Leu Leu Gly Glu Leu Ser Arg Lys Gln Glu Ser Asp
        50                  55                  60

Trp Val Ser Val Val Met Gln Val Met Glu Leu Glu Ser Ser Ser Lys
65                  70                  75                  80

His Met Glu Ser Arg Leu Ser Thr Ala Glu Ser Lys Tyr Ser Glu Met
                85                  90                  95

Asn Asn Gln Ile Asp Ile Met Gln Leu Gln Ala Ala Gln Thr Val Thr
```

-continued

```
                    100                 105                 110
Gln Thr Ser Ala Asp Ala Ile Tyr Asp Cys Ser Ser Leu Tyr Gln Lys
            115                 120                 125

Asn Tyr Arg Ile Ser Gly Val Tyr Lys Leu Pro Pro Asp Glu Phe Leu
            130                 135                 140

Gly Ser Pro Glu Leu Glu Val Phe Cys Asp Met Glu Thr Ser Gly Gly
145                 150                 155                 160

Gly Trp Thr Ile Ile Gln Arg Arg Lys Ser Gly Leu Val Ser Phe Tyr
                165                 170                 175

Gln Asp Trp Arg Gln Tyr Lys Gln Gly Phe Gly Ser Ile Arg Gly Asp
            180                 185                 190

Phe Trp Leu Gly Asn Glu His Ile His Arg Leu Thr Arg Gln Pro Ser
            195                 200                 205

Arg Leu Arg Val Glu Leu Glu Asp Trp Glu Gly Asn Ala Arg Tyr Ala
            210                 215                 220

Glu Tyr Ser Tyr Phe Ala Leu Gly Asn Glu Leu Asn Ser Tyr Arg Leu
225                 230                 235                 240

Phe Leu Gly Asn Tyr Ser Gly Asn Val Gly Lys Asp Ala Leu Leu Tyr
                245                 250                 255

His Asn Asn Thr Val Phe Ser Thr Lys Asp Lys Asp Asn Asp Asn Cys
            260                 265                 270

Leu Asp Lys Cys Ala Gln Leu Arg Lys Gly Gly Tyr Trp Tyr Asn Cys
            275                 280                 285

Cys Thr Asp Ser Asn Leu Asn Gly Val Tyr Tyr Arg Leu Gly Glu His
            290                 295                 300

Arg Lys His Met Asp Gly Ile Ser Trp Tyr Gly Trp His Gly Ala Asn
305                 310                 315                 320

Tyr Ser Leu Lys Arg Val Glu Met Lys Ile Arg Pro Glu Ala Phe Lys
                325                 330                 335

Pro
```